(12) United States Patent
O'Connor et al.

(10) Patent No.: US 6,773,823 B2
(45) Date of Patent: Aug. 10, 2004

(54) SEQUENTIAL SYNTHESIS OF CORE-SHELL NANOPARTICLES USING REVERSE MICELLES

(75) Inventors: Charles J. O'Connor, New Orleans, LA (US); Everett E. Carpenter, Washington, DC (US); Jessica Ann Sims, Slidell, LA (US)

(73) Assignee: University of New Orleans Research and Technology Foundation, Inc., New Orleans, LA (US)

( * ) Notice: Subject to any disclaimer, the term of this patent is extended or adjusted under 35 U.S.C. 154(b) by 268 days.

(21) Appl. No.: 09/829,401

(22) Filed: Apr. 9, 2001

(65) Prior Publication Data

US 2002/0068187 A1 Jun. 6, 2002

Related U.S. Application Data

(60) Provisional application No. 60/196,008, filed on Apr. 7, 2000.

(51) Int. Cl.[7] .................................................. B32B 5/16
(52) U.S. Cl. ....................... 428/548; 428/570; 428/590; 428/403; 428/900
(58) Field of Search ............................... 428/544, 548, 428/570, 590, 403, 900

(56) References Cited

U.S. PATENT DOCUMENTS

| | | | | |
|---|---|---|---|---|
| 4,309,457 A | * | 1/1982 | Kawasumi et al. | 427/214 |
| 5,770,172 A | * | 6/1998 | Linehan et al. | 423/561.1 |
| 5,879,715 A | * | 3/1999 | Higgins et al. | 424/489 |
| 6,022,500 A | * | 2/2000 | John et al. | 264/4.1 |
| 6,045,925 A | * | 4/2000 | Klabunde et al. | 428/548 |
| 6,126,740 A | * | 10/2000 | Schulz et al. | 117/4 |
| 6,294,401 B1 | * | 9/2001 | Jacobson et al. | 438/99 |
| 6,344,272 B1 | * | 2/2002 | Oldenburg et al. | 428/403 |
| 6,413,489 B1 | * | 7/2002 | Ying et al. | 423/600 |
| 6,514,481 B1 | * | 2/2003 | Prasad et al. | 424/9.32 |
| 6,548,264 B1 | * | 4/2003 | Tan et al. | 435/7.21 |

* cited by examiner

*Primary Examiner*—H. Thi Le
(74) *Attorney, Agent, or Firm*—Garvey,Smith,Nehrbass & Doody, L.L.C.; Seth M. Nehrbass

(57) ABSTRACT

By utilizing the sequential synthesis afforded reverse micelles, nanocomposite materials can be synthesized which have a diamagnetic core surrounded by a thin shell of ferromagnetic material passivated with a second shell of a diamagnet. Using gold as the diamagnetic material and iron as the ferromagnetic material, nanocomposites can be synthesized where there is a thin layer of the magnetic material, which is passivated and protected from oxidation. In this case, all of the spins of the magnetic layer lie within the surface of the particle.

30 Claims, 5 Drawing Sheets

SEQUENTIAL SYNTHESIS OF CORE-SHELL NANOPARTICLES USING REVERSE MICELLES

CROSS-REFERENCE TO RELATED APPLICATIONS

Priority of U.S. Provisional Patent Application Serial No. 60/196,008, filed Apr. 7, 2000, incorporated herein by reference, is hereby claimed.

STATEMENT REGARDING FEDERALLY SPONSORED RESEARCH OR DEVELOPMENT

This work was supported by DARPA grant no. MDA972-97-1-0003. The government may have rights in this invention.

REFERENCE TO A "MICROFICHE APPENDIX"

Not applicable

BACKGROUND OF THE INVENTION

1. Field of the Invention

The present invention relates to nanocomposites. More particularly, the present invention relates to a method of producing nanocomposites using reverse micelles and to the nanocomposites so formed.

2. General Background of the Invention

Present technology is reaching the limit of usefulness due to the small sizes required. As a result, new synthetic methods are being used to synthesize materials. It has been shown that granular Fe/Au and Co/Au alloys synthesized using traditional ball milling methods have an improved GMR effect over thin-films. Studies by others have elucidated the role of surface spins in the origins of GMR while uniformity has also been demonstrated as key. Present technology is limited due to scalability and versatility.

In ferrofluid applications and biochemical applications, the current technology is limited due to magnetic field required and the size of the particles involved.

The following U.S. patents are incorporated herein by reference:
U.S. Pat. Nos. 5,879,715; 5,889,091.

BRIEF SUMMARY OF THE INVENTION

The present inventors have made a nanocomposite comprising a diamagnetic core of a material from the group consisting of gold, silver, copper, and platinum; a thin layer of magnetic material from the group consisting of iron and cobalt and alloys (including platinum alloys) containing iron and/or cobalt, formed on the diamagnetic core; a passivating layer of diamagnetic material from the group consisting of gold, silver, platinum, and copper, and alloys containing these materials, formed on the layer of magnetic material. In a preferred example, the diamagnetic core is made of gold, the magnetic material is made of iron, and the passivating layer is made of gold.

The present invention comprises a method of producing nanocomposites and the nanocomposites so produced.

Reverse micelles have been proven useful as nano-reactors for the growth of metal colloids. The present inventors have adapted the process to sequentially grow first a magnetic core material (either Iron or Cobalt) and then the surface is coated with a diamagnetic coating. This techniques has several advantages over current methods:

Reverse micelles technique forms more uniform size and shaped particles, which is essential in current semiconductor and computer applications.

It is easily scalable, so the reaction can be modified for the generation of large quantities of nanoparticles.

The high uniformity in the particles allows for improved magnetic and electronic properties.

The presence of the diamagnetic coating passivates the magnetic core thus protecting the magnetic properties without having a pronounced effect on the magnetic properties.

The presence of the diamagnetic coating allows for a surface that can be derivatized to allow for greater versatility while not reducing the magnetic properties.

This process can be modified to form stable nanoparticles of iron or cobalt useful in a variety of applications ranging from ferrofluids to granular GMR materials.

Possible areas in which this invention can be used commercially are in the semiconductor industry for novel inductor materials, as well as in the computer industry where it potentially could be used as an innovative storage media. Material synthesized in this fashion could also be used as giant magnetoresistance (GMR) sensors, which have application in a wide variety of applications from automobiles to computers.

The stability of the surfactant coated metal colloids allows for the creation of ferrofluids, which are usable applications from petrochemical industry to consumer electronics. The biocompatability of the granular materials also allows for potential uses as directed drug delivery and targeted sensing for in vivo applications.

In ferrofluid applications and biochemical applications, the current technology is limited due to magnetic field required and the size of the particles involved. By using nanocomposite materials synthesized in this fashion, the enhanced magnetic properties of metals can be used while remaining chemically inert.

The present invention also comprises an innovative giant magnetoresistance (GMR) material.

The present inventors have modified a reverse micelle synthesis technique to generate an innovative giant magnetoresistance material. Using cetyltrimethylammonium bromide, n-butanol, octane and aqueous reactants, the present inventors have been able to synthesize an inventive new nanocomposite. The composite has a gold core onto which a thin layer of iron is grown, which is then passivated with gold. These composites, which the present inventors have dubbed "nano-onions", have several advantages over traditional GMR materials. 1) The materials were synthesized using the reverse micelle technique, which has numerous advantages over standard methods. 2) The material has a drastically increased surface area and thus a larger GMR response is measured compared to other materials of similar composition. 3) The presence of gold allows for greater functionality and protection of the magnetic component. 4) This is the first material of its type that has been synthesized using the reverse micelle technique.

Present technology is reaching the limit of usefulness due to the small sizes required. As a result, new synthetic methods are being used to synthesize materials. It has been shown that granular Fe/Au and Co/Au alloys synthesized using traditional ball milling methods have an improved GMR effect over thin-films. Studies by others have elucidated the role of surface spins in the origins of GMR while uniformity has also been demonstrated as key. Since the method of the present invention generates materials that have a significantly higher degree of uniformity as well as a dramatically larger percentage of surface spins, they display a larger GMR effect over materials with similar compositions. Present technology is limited due to scalability and versatility.

By utilizing the sequential synthesis afforded reverse micelles, nanocomposite materials can be synthesized which have a diamagnetic core surrounded by a thin shell of ferromagnetic material passivated with a second shell of a diamagnet. Using gold as the diamagnetic material and iron as the ferromagnetic material, nanocomposites can be synthesized where there is a thin layer of the magnetic material, which is passivated and protected from oxidation. In this case, all of the spins of the magnetic layer lie within the surface of the particle.

Magnetic properties were measured for nanophase particles using SQUID magnetometry. The particles, which consist of a 6 nm core of gold, coated with a 1 nm thick iron layer and passivated with an outer shell of gold, are superparamagnetic with a blocking temperature of 45 K and coercivity at 10 K of 400 Oe. These results are similar to magnetic properties of 8 nm iron particles coated with gold, where blocking temperature is 50 K and coercivity is 400 Oe. This suggests that in nanoparticles the spins that define the outer surface are responsible for the magnetic properties.

BRIEF DESCRIPTION OF THE SEVERAL VIEWS OF THE DRAWINGS

For a further understanding of the nature, objects, and advantages of the present invention, reference should be had to the following detailed description, read in conjunction with the following drawings, wherein like reference numerals denote like elements and wherein.

DETAILED DESCRIPTION OF THE INVENTION

Introduction

Figure 1:
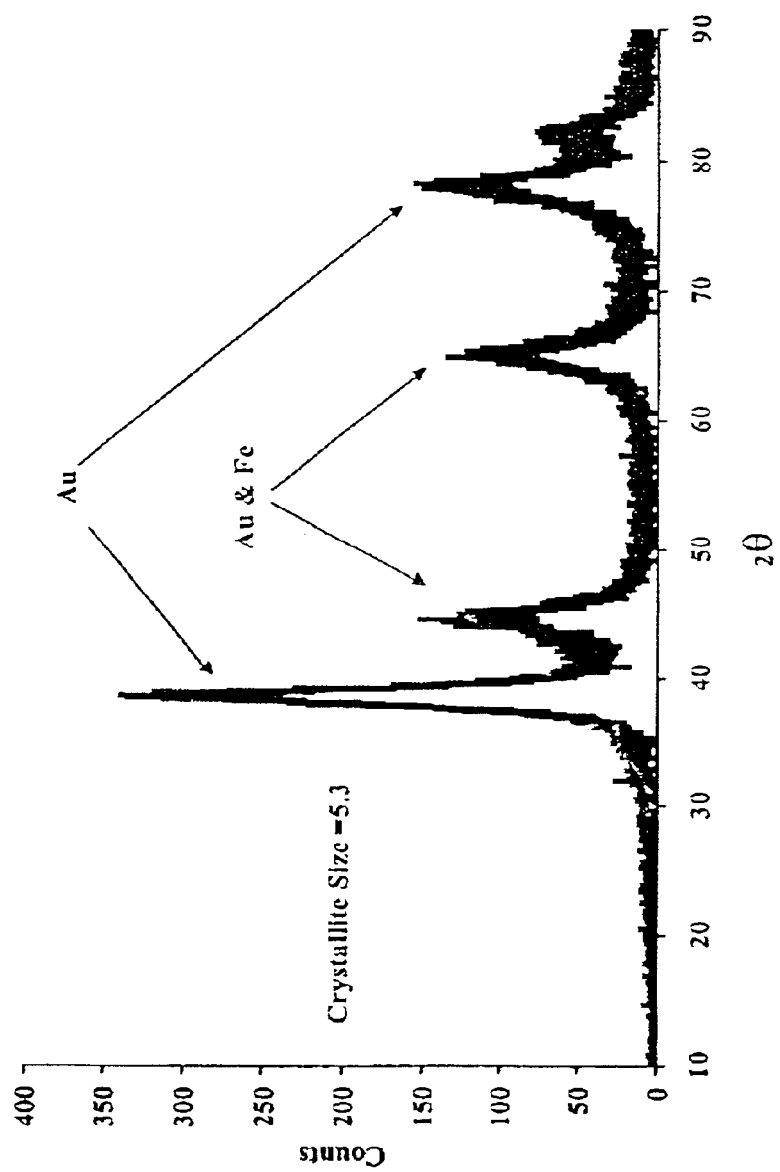
FIG. 1 is a representative X-ray powder diffraction pattern taken using a Phillips-EXPERT diffractometer with a graphite monochromator and PMT detector.

Nanoparticles are characterized by their high surface to volume ratio. Minute changes in the surface layer have a pronounced effect on the overall magnetization of the nanoparticles[1]. Studying the magnetization of the surface layers of nanoparticle is very difficult due to many factors, mainly the lack of experimental methods to grow core-shell structures. Previous attempts to study the surface layer of nanoparticles rely on the change in the magnetic properties after surface modification.[2,3] We have devised an experiment by which we can synthesize an onion-like structure where there exists a thin shell of iron spaced between a gold core and shell simulating the surface layer. In this case the contribution to magnetic properties is removed by using a diamagnetic core material.

Using reverse micelles as constrained reactors we synthesized gold-iron nano-onion like structures. Iron is a well studied system in which the surface effects are well documented. Gold was used as core and coating since it is immiscible with iron therefore there is less likely alloying at the interfaces. The gold shell on the surface has proved effective at preventing oxidation of the iron. The microemulsion was prepared using a quaternary surfactant system of cetyltrimethylammonium bromide (CTAB), n-butanol, n-octane, and water.[4] The aqueous reactants were introduced into the micelle solution and allowed to react[5] within the confines of the micelles. The micelle synthesis method leads to very uniform spherical particles of sizes determined by the ω, the molar ratio of surfactant to water.[6] This method allows the synthesis of iron particles that then can be used as a nucleation source for the epitaxial growth of a gold shell.[7] The oxidation of the metal core by air is inhibited by the presence of a gold coating. In the case of 8 nanometer iron nanoparticles without a gold coating, the nanoparticles are pyrophoric and oxidize immediately upon coming into contact with air.[8] However, the presence of a gold coating inhibits oxidation and allows the particles to be air stable.

Experimental

The synthesis of core-shell structures was accomplished using a sequential synthesis technique afforded by reverse micelles. This procedure was carried out in three steps. All reverse micellar solutions were prepared using cetyltrimethylammonium bromide (CTAB) as the surfactant with n-octane as the oil phase. N-Butanol was used as a co-surfactant, increasing the polarity of the surfactant and helping to stabilize the micelle solutions. Aqueous reactants of hydrogen tetrachloroaurate, sodium borohydride, and ferrous sulfate were used to form the reverse micelle. The size of the particles was controlled by molar ratio of the surfactant to water (ω=[$H_2O$]/[CTAB]). All chemicals were purchased from Aldrich Chemical Company (Milwaukee, Wis.) and used without further purification. Water used in the synthesis was distilled and deionized and passed through a 0.5-micron filter.

In step one, two micelle solutions were prepared using 0.1M $HAuCl_4$ (aq) and the other with 0.6M $NaBH_4$ (aq). The molar ratio ω=6 was used to prepare a 6 nanometer diameter core of gold. These solutions were mixed together using a magnetic stirrer and allowed to react for 2 hours. To ensure that all the gold was reduced the reaction was carried out in the presence of long wave ultra-violet (uv) light. After two hours the micelle solution was the characteristic clear red solution expected for a gold colloid. In preparation for step two, the reaction was also carried out under flowing argon gas.

In step two the first shell of iron was synthesized. Two additional micelle solutions were prepared using 0.1 M $FeSO_4$ and 0.6 M $NaBH_4$ respectively. These solutions were degassed and added to the reaction mixture. In this case, the $NaBH_4$ solution was prepared slightly larger to expand the micelles to ω=8 within the reaction mixture to allow for the growth of a one nanometer thick shell. The solution turned black upon the addition of the iron. The reaction was stirred under flowing argon for 2 hours.

The second shell was prepared in a similar fashion to the first. Two additional micelles were prepared using 0.1M HAuCl$_4$ and 0.6M NaBH$_4$. Once again the NaBH$_4$ was made slightly larger to ω=12 to accommodate a two nanometer thick gold shell. The solutions were again allowed to react for 2 hours in the presence of UV light and under flowing argon.

The micelles in the reaction mixture were disrupted using acetone causing the nanoparticles to precipitate. Repeated washings using a 1:1 mixture of chloroform/methanol removed the surfactant. The iron containing particles were removed from those particles which did not contain iron using a permanent magnet (5000 Oe). The nanoparticles were dried under vacuum, resulting in a black powder. Upon pressing the powder for electronic measurements, the materials took on a metallic gold sheen. After passivation with the second coating of gold, the particles became air stable with no oxidation detectable in the magnetic data after six weeks.

Characterization

Elemental analysis on the sample was carried out using an energy dispersive spectroscopy (EDS) attachment on a JEOL 2010 transmission electron microscope. If all the iron were incorporated in the thin shell as expected, there should be 5% mole fraction of iron present in the particles. EDS measurements show a slightly higher percentage at 10% (+4%). This slight variance could arise due to a small amount of non-iron containing nanoparticles which were trapped during the clean-up phase.

Figure 2:
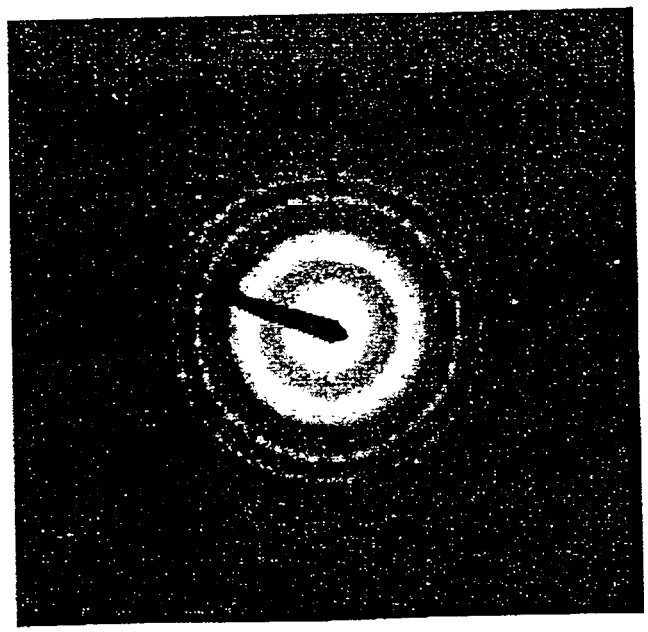
FIG. 2 is a selected area microdiffraction pattern taken with a 2 nm focused electron beam; the concentric rings represent the high crystallinity in the nano-onion.

Structural characterization was carried out using X-ray powder diffraction and electron microdiffraction. X-ray diffraction on the powdered sample was performed using a Phillips-Norelco X-Ray diffractometer with a graphite monochromator and PMT detector. A representative XRD plot of the sample is presented in FIG. 1. The peaks in the pattern can be indexed to the reference pattern of fcc gold. The pattern for a bcc iron is obscured under the gold. During extended scan times, the overlapping peaks begin to separate, but to due to the extended times needed to resolve iron from gold, XRD is used to confirm the presence of gold. This conclusion is also confirmed in the electron diffraction patterns presented in FIG. 2, where there is a diffusion of the rings due to a slight mismatch between the overlapping of 200, and 220 of the fcc gold diffusion rings with 110, and 220 of the bcc iron rings. Although diffraction studies cannot differentiate between iron and gold in the system, they do demonstrate a high degree of crystallinity and uniformity in the particles. The peak location can be indexed to that of fcc gold structure.

Figure 3:
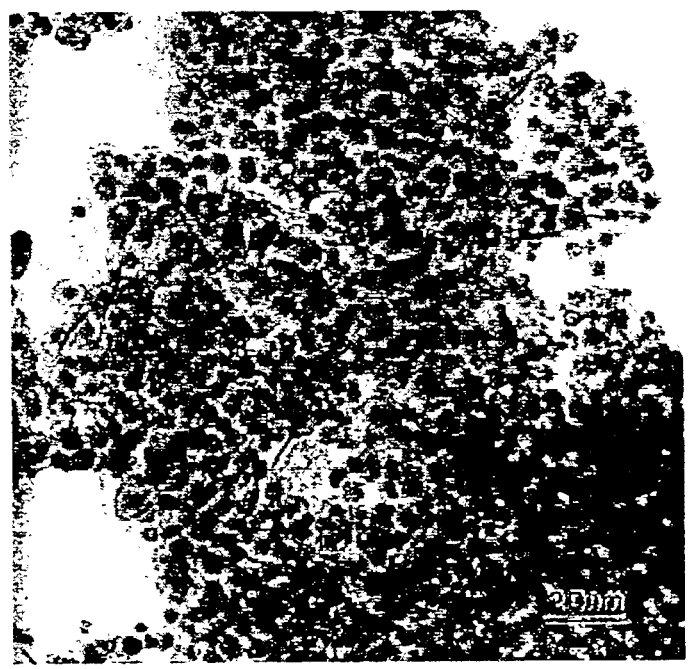
FIG. 3 is a representative micrograph taken using a JEOL 2010 transmission electron microscope.

Morphology was determined using transmission electron microscopy. A representative micrograph is presented in FIG. 3. In the micrograph the particles are clearly spherical and are on average 12 nanometers. The particles have a narrow size distribution common to the microemulsion techniques. One of the more noteworthy features on the micrograph is the presence of the shell structure revealed as concentric rings on the particles. This shell structure could be coming from three sources, i.e., first sample focus, surfactant contamination, and/or from the difference in the electron density of the iron and gold. To discount the first option, the granularity substrate can be seen clearly. During over focus and under focus the shell remains. If the shell structure were solely an artifact of the focus or sample preparation, the shells would have vanished when out of focus. EDS proved useful in discounting the second possibility, the presence of surfactant. EDS measurements were taken with the electron beam focused down to 2 nm only on the shell, on gold and iron were present. If the surfactant had been the cause of the shell structure, then there would have been additional counterions (sulfates or bromides etc.) present to balance the charge on the CTAB. EDS measurements on the shell along presented no additional elements present, just gold and iron. In addition, the ratios of gold to iron change as the electron beam is focused across the shell, suggesting the higher concentration of iron present in the shell versus the core.

Magnetic Measurements

Figure 4:
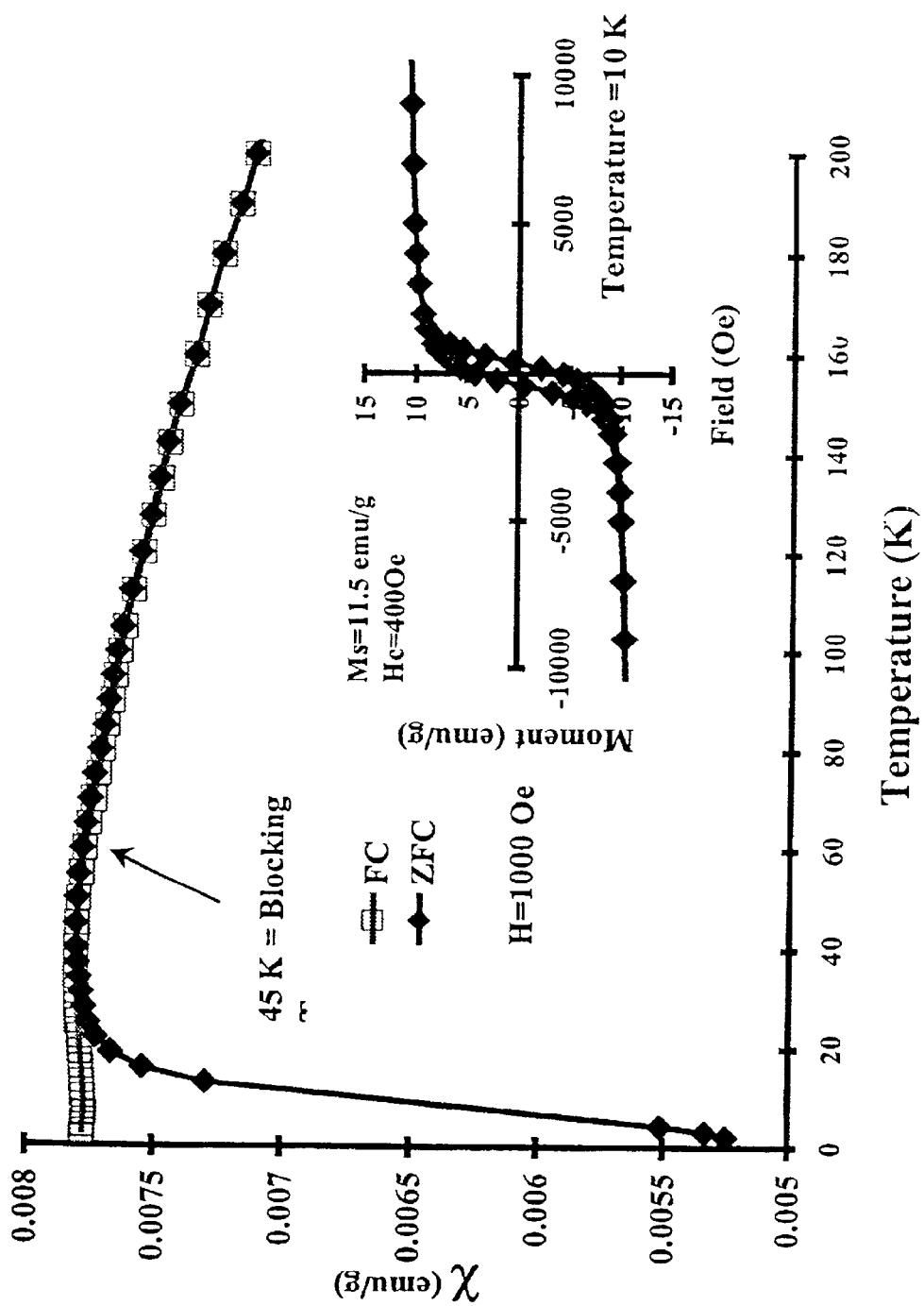
FIG. 4 shows magnetic susceptibility versus temperature with an applied measuring field of 1000 Oe; the inset represents the magnetization curve taken at 10K.

A Quantum Design MPMS 5 SQUID magnetometer was used for the magnetization measurements. A representative magnetic susceptibility plot, presented in FIG. 4, exhibits a cusp in the zero field cooled (ZFC) susceptibility at 52K corresponding to a blocking temperature, TB. Above TB, in the superparamagnetic regime, the particles are free to align with the field during the measuring time and depart from the ZFC susceptibility at a temperature near the ZFC maxima and increases below this temperature.

Below the temperature where the nano-onions have superparamagnetic behavior, the nanomaterials reveal a remanent magnetization and coercivity. The inset of FIG. 4 records the magnetization of the Au/Fe/Au sample as the magnetic field of the susceptometer cycles between +50 kOe and −50 kOe. Above the blocking temperature, in the superparamagnetic regime, no coercivity or remanence is observed. At 10K, the coercivity is 420 Oe while the remanence is 3.65 emu/g. The saturation magnetization of the particles is 11.5 emu/g, corresponding to that expected for a bulk iron sample. These values indicate a high degree of orientation of the nanoparticles about the easy axis of magnetization. Theoretical maximum values for an isotropic iron system are 165 Oe while the values for an aligned anisotropic system are 525 Oe. Since the values lie close to that of an aligned system, a high degree of ordering can be assumed.

An interesting comparison can be made between nano-onions and simpler gold-coated iron nanocomposites also synthesized in reverse micelles. The blocking temperature in 8 nm iron particles coated with 2 nanometers of gold is also 52 K and coercivity is also 420 Oe which, after adjusting for the amount of iron present, are equal to those of the nano-onions. These results help to support the conclusion that blocking temperature and coercivity in core-shell nanoparticles are dominated by intraparticle coupling of the spins on the surface of the particles.[9] In the nano-onion system only surface spins are present.

Dynamic susceptibility measurements at radio frequencies were done using a novel resonant method based on a tunnel-diode oscillator (TDO) operating at 5 MHz. The Au—Fe—Au nano-onions in powder form are placed in gelcaps that snugly fit into the core of the inductive copper coil (L). This is inserted into the sample space of a commercial Physical Property Measurement System (PPMS) from Quantum Design using a customized radio-frequency (RF) co-axial probe. The temperature (T) and static magnetic field (H) are varied using the PPMS. The oscillating RF field ($H_{rf}$) produced by the RF current flowing in the coil windings, is oriented perpendicular to the static field H and this arrangement sets up the transverse modulation geometry. In the experiment, the measured quantity is the shift in resonant frequency as the static field is varied. The frequency shift (Δω) arises from a change in coil inductance (ΔL) and that in turn gives an accurate measure of the variation in the real part of the transverse susceptibility, $\Delta\chi_t$.

Figure 5:
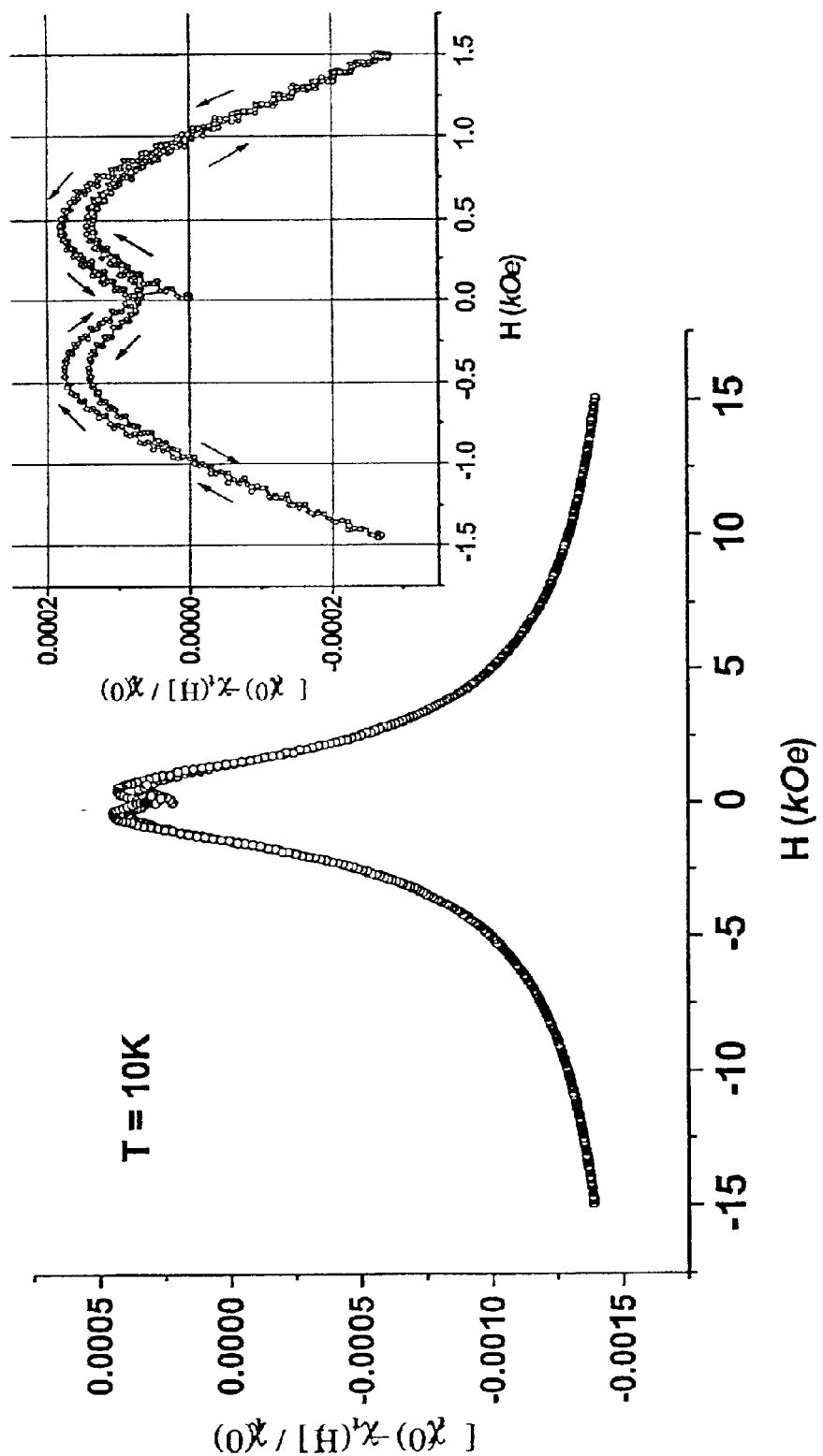
FIG. 5 shows dynamic transverse susceptibility of the Au—Fe—Au nano-onions measured using the RF TDO method; the inset represents the low-field hysteresis and peak structure in the dynamic susceptibility; the arrows represent the direction as the field is ramped through a full cycle: 0→1.5 kOe→−1.5 kOe→1.5 kOe→0.

The measured change in transverse susceptibility, $[\chi_t(0)-\chi_t(H)]/\chi_t(0)$, as H is varied up to 15 kOe is shown in FIG. 5. This is at a temperature of 10 K which is well below the blocking temperature. Peaks in the data, located roughly symmetric about zero can be seen at low fields and the overall variation resembles a bell-shaped curve. Hysteresis can also be clearly made out in the vicinity of the low field peaks. Note that the high density of data points and smooth nature of the curve showcases the precision achieved by our RF method that is not obtained in other experiments. This can directly be ascribed to the nature of this resonance technique and the high sensitivity, i.e. the ability to detect changes of a few Hz in 5 MHz.

To map out the low-field hysteresis and study the peaks in finer detail, we started at zero field and cycled H up and down between 1500 and −1500 Oe. The dynamic susceptibility change is plotted in the inset of FIG. 5.

The peak structure and hysteresis systematics are now clearly visible. As H is varied over the entire loop cycle, two observations can be made about the peak structure—(a) symmetric location around ±0.5 kOe and (b) asymmetric peak heights as the field is swept in one direction from −1.5 kOe→1.5 kOe or vice versa (follow arrows in FIG. 4). As to the asymmetry in peak heights, the argument can be made as follows. When the field is cycled from positive to negative, as a consequence of remanence, the segment of the M-H curve in the first quadrant (H>0) is shorter with a smaller slope than the section in the second and third quadrants (H<0). Likewise, when the field is changed from negative to positive, the third quadrant segment (H<0) is shorter than the one in the fourth and first quadrants (H>0) as zero field is crossed. This asymmetry is directly reflected in the asymmetric peak heights seen in the RF data.

Electronic Measurements

A Quantum Design Physical Property Measurement System (PPMS) was used to investigate the electronic properties of the materials. The samples were cold pressed to form pellets to which electrical contacts were made. All electrical measurements presented in this study utilized the standard van der Paw, 4 point square, geometry.[10] The temperature dependent resistivity in zero magnetic field is presented in FIG. 6. Between 300 K and 180 K the system shows typical metallic behavior as the resistivity falls with decreasing temperature. At lower temperatures, the resistivity unexpectedly rose. It is postulated that the first rise at approximately 100 K is due to a finite size effect where there is a transition from itinerant electrons to Anderson localized electrons. At this point the electrons are constrained to scattering between the Fe shells. The lower increase in resistivity, at approximately the blocking temperature, is believed to be due to a similar effect. At this point it is believed that the scattering events cause the electrons to be constrained within the Fe shells. From these results, it is seen that such nano-onion composites are suitable for further experimental studies of Anderson localization.

Figure 6:
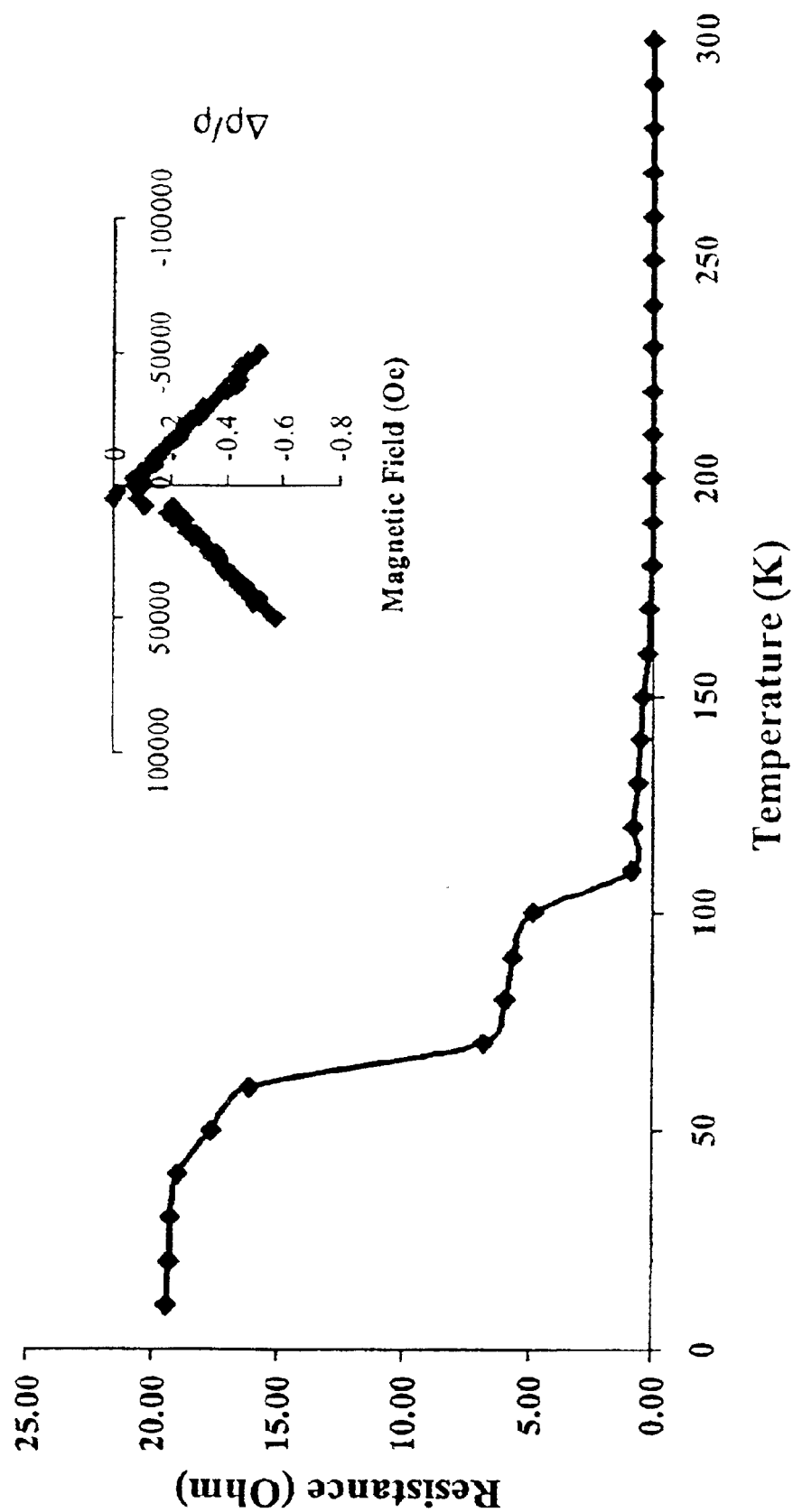
FIG. 6 show resistivity verses temperature taken in zero applied field; the inset represents a change in resistivity as a function of magnetic field at 10K.

The magnetoresistance of the materials was investigated at all temperatures. At higher temperatures, the thermal component of the intrinsic low resistivity of the sample dominates. Consequently, at room temperature, experimental measurement of the magnetic component of the resistivity was not possible. It was possible to accurately measure the magnetoresistance at 10 K, as shown in the inset of FIG. 6. The MR at 10K in a 5 T perpendicular field is $\Delta\rho/\rho$=0.5%. While such a figure is low, it should be noted that this system contains only 5% by mass Fe. When compared to studies of conventional GMR in granular Fe/Au,[11] it is seen that this figure is actually slightly greater than previous work.

Conclusion

The microemulsion technique provides for a versatile method for the synthesis of nano-onion like gold-iron-gold co-shell nanoparticles. The increase in the surface area provides for greater spin scattering which, at temperatures below the blocking temperature, results in a greatly increased resistance. The high uniformity of sizes leads to a higher MR response than previously reported in similar composition materials. This expanded microemulsion technique provides a unique method to generate particles for the study of Anderson localized electrons, as well as a method to study the magnetization of nanoparticles.

The nanocomposites are preferably annealed to increase coercivity. They are preferably annealed at a temperature of about 300 K.

Acknowledgements

We would like to thank Jinke Tang for many discussions about electronic characterization. This work was supported by DARPA grant no. MDA972-97-1-0003.

REFERENCES

All of Which are Incorporated Herein by Reference

1) Bodker, F.; Morup, S.; Linderoth, S. *Physical Review Letters* 1994, 72, 282–285.
2) Zaluska-Kotur, M. A. *Physical Review B* 1996, 54, 1064–1071.
3) Pardavi-Horvath, M.; Zheng, G.; Vertesy, G.; Magni, A. *IEEE Transactions on Magnetics* 1996, 32, 4469–4471.
4) Attwood, D.; Mosquera, V.; Rodriguez, J.; Garcia, M.; Suarez, M. J. *Colloid and Polymer Science* 1994, 272, 584–591.
5) Glavee, G. N.; Kernizan, C. R.; Kalbunde, K. J.; Sorensen, C. M.; Hadjapanayis, G. C. *Chemistry of Materials* 1991, 3, 967–976.
6) Boutonnet, M.; Kizling, J.; Stenius, P. *Colloids and Surfaces A: Physicochemical and Engineering Aspects* 1982, 5, 209–225.
7) Prozorov, T.; Prozorov, R.; Gedanken, A. *Advanced Materials* 1998, 10, 1529–1532.
8) Klabunde, K. J.; Zhang, D.; Glavee, G. N.; Sorensen, C. M. *Chemistry of Materials* 1994, 6, 784–787.
9) Carpenter, E. E.; Sangregorio, C.; O'Connor, C. J. *IEEE Transactions on Magnetics* Vol. 35, No. 5, pages 3496–3498 (September 1999).
10) Wieder, H. H. *Laboratory notes on Electrical and Galvanomagnetic Measurements*; Elsevier: 1979.
11) Wang, J. Q.; Xiao, G. *Physical Review B* 1994, 49, 3982.

More information about the present invention can be found in the following papers, all of which are incorporated herein by reference:

Carpenter, Everett E., and Amar Kumbhar, Joan A. Wiemann, Hariharan Srikanth, Jason Wiggins, Weilie Zhou and Charles J. O'Connor, "Synthesis and Magnetic Properties of Gold-Iron-Gold Nano-composites," *Mater. Sci. Eng.*, A, A286 (1), 81–86 (2000) (draft attached to U.S. Provisional Patent Application Serial No. 60/196, 008);

Carpenter, Everett E., and Claudio Sangregorio and Charles J. O'Connor, "Effects of Shell Thickness on Blocking Temperature of Nanocomposites of Metal Particles with Gold Shells", *IEEE Transactions on Magnetics*, Vol. 35, No. 5, pages 3496–3498 (September 1999) (copy attached to U.S. Provisional Patent Application Serial No. 60/196, 008); and Zhou, W. L., and E. E. Carpenter, J. Sims, A. Kumbhar, and C. J. O'Connor, "Transmission Electron Microscopy Study of Gold-coated Iron Core-shell and Au/Fe/Au Onion-like Nanoparticles Synthesized Using Reverse Micelles," *Mater. Res. Soc. Symp. Proc.*, 581 (Nanophase and Nanocomposite Materials III), 107–112 (2000) (draft attached to U.S. Provisional Patent Application Serial No. 60/196,008);

O'Connor, Charles J., and Vladimir Kolesnichenko, Everett Carpenter, Claudio Sangregorio, Weilie Zhou, Amar Kumbhar, Jessica Sims, Fabrice Agnoli, "Fabrication and Properties of Magnetic Particles with Nanometer Dimensions", Synthetic Materials (copy attached—in press);

Kumbhar, Amar, and Leonard Spinu, Fabrice Agnoli, Kai-Ying Wang, Weilie Zhou, Charles J. O'Connor, "Magnetic properties of cobalt and cobalt-platinum alloy nanoparticles synthesized via microemulsion technique", presented at the 8th Joint MMM-Intermag Conference, San Antonio, Tex., Jan. 7–11, 2001 (copy of draft attached); and O'Connor, Charles J., and Jessica A. Sims, Amar Kumbhar, Vladimir L. Kolesnichenko, Weilie L. Zhou and Joan A. Wiemann, "Magnetic properties of FePtX/Au and CoPtX/Au core-shell nanoparticles", JMMM (copy attached—in press).

Carpenter, E. E., and J. A. Sims, J. A. Wienmann, W. L. Zhou, and C. J. O'Connor, "Magnetic properties of iron and iron platinum alloys synthesized via microemulsion techniques", J. App. Physics 87, No. 9, pp. 5615–5617 (May 1, 2000)—(copy attached).

All measurements disclosed herein are at standard temperature and pressure, at sea level on Earth, unless indicated otherwise. All materials used or intended to be used in a human being are biocompatible, unless indicated otherwise.

The foregoing embodiments are presented by way of example only; the scope of the present invention is to be limited only by the following claims.

What is claimed is:

1. A nanocomposite comprising:
a diamagnetic core;
a layer of magnetic material fanned on the diamagnetic core;
a passivating layer of diamagnetic material formed on the layer of magnetic material.

2. The nanocomposite of claim 1, wherein:
the layer of magnetic material is thin.

3. The nanocomposite of claim 1, wherein:
the diamagnetic core is a material from the group consisting of gold, silver, copper, and platinum;
the magnetic material is a material from the group consisting of iron and cobalt and alloys containing iron and/or cobalt;
the passivating layer is a material from the group consisting of gold, silver, platinum, and copper, and alloys containing these materials.

4. The nanocomposite of claim 3, wherein:
the layer of magnetic material is thin.

5. The nanocomposite of claim 1, comprising:
a gold core;
a thin layer of iron formed on the gold core;
a passivating layer of gold on the layer of iron.

6. The nanocomposite of claim 5, wherein:
the layer of magnetic material is thin.

7. The nanocomposite of claim 1, produced with a reverse micelle synthesis technique.

8. The nanocomposite of claim 7, wherein:
the layer of magnetic material is thin.

9. The nanocomposite of claim 1, synthesized using cetyltrimethylammonium bromide, n-butanol, octane and aqueous reactants.

10. The nanocomposite of claim 9, wherein:
the layer of magnetic material is thin.

11. The nanocomposite of claim 1, wherein:
the diamagnetic core is a material from the group consisting of gold, silver, copper, and platinum;
the magnetic material is a material from the group consisting of iron and cobalt and platinum alloys containing iron and/or cobalt;
the passivating layer is a material from the group consisting of gold, silver, platinum, and copper, and alloys containing these materials.

12. The nanocomposite of claim 11, wherein:
the layer of magnetic material is thin.

13. The nanocomposite of claim 1, wherein the nanocomposite is annealed.

14. The nanocomposite of claim 13, wherein:
the layer of magnetic material is thin.

15. The nanocomposite of claim 13, wherein the nanocomposite is annealed at a temperature of about 300 K.

16. The nanocomposite of claim 15, wherein:
the layer of magnetic material is thin.

17. Ferrofluids made with the nanocomposite of claim 1.

18. The ferrofluids of claim 17, wherein:
the layer of magnetic material is thin.

19. Granular GMR materials made with the nanocomposite of claim 1.

20. The granular GMR materials of claim 19, wherein:
the layer of magnetic material is thin.

21. Inductor materials made with the nanocomposite of claim 1.

22. The inductor materials of claim 21, wherein:
the layer of magnetic material is thin.

23. Storage media made with the nanocomposite of claim 1.

24. The storage media of claim 23, wherein:
the layer of magnetic material is thin.

25. Giant magnetoresistance sensors made with the nanocomposite of claim 1.

26. The giant magnetoresistance sensors of claim 25, wherein:
the layer of magnetic material is thin.

27. Directed drug delivery agents made with the nanocomposite of claim 1.

28. The directed drug delivery agents of claim 27, wherein:
the layer of magnetic material is thin.

29. Agents for targeted sensing for in vivo applications made with the nanocomposite of claim 1.

30. The agents of claim 29, wherein:
the layer of magnetic material is thin.

* * * * *